United States Patent

Scheifinger et al.

Patent Number: 5,679,349
Date of Patent: Oct. 21, 1997

[54] VACCINE DESIGN AND PRODUCTION

[75] Inventors: Curtis C. Scheifinger, Morristown; David L. Smiley, Greenfield, both of Ind.

[73] Assignee: Eli Lilly and Company, Indianapolis, Ind.

[21] Appl. No.: 678,444

[22] Filed: Jul. 3, 1996

Related U.S. Application Data

[63] Continuation of Ser. No. 147,765, Nov. 5, 1993, abandoned.

[51] Int. Cl.$^6$ .................. A61K 39/02; A61K 39/085
[52] U.S. Cl. .................. 424/190.1; 424/243.1; 424/823; 530/326
[58] Field of Search .................. 424/190.1, 243.1, 424/823; 530/326

[56] References Cited

FOREIGN PATENT DOCUMENTS

93/14198  7/1993  WIPO.

OTHER PUBLICATIONS

Frost, A. J., Selective Adhesion of Microorganisms to the Ductular Epithelium of the Bovine Mammary Gland. *Infection and Immunity*, vol. 12, No. 5, pp. 1154–1156, 1975.

Olmsted, S. B. and Norcross, N. L. Bacterial Adherence of *Staphylococcus aureus* to Bovine Mammary Epithelial Cells in Culture. *Abstract 48, International Symposium Virulence Mechanisms of Veterinary Bacterial Pathogens*, Iowa State University, 1987.

Olmsted, S. B. and Norcross, N. L. Effect of Specific Antibody on Adherence of *Staphylococcus aureus* to Bovine Mammary Epithelial Cells, Infection and Immunity, vol. 60, pp. 249–256, 1992.

J.P. Caffin, et al., J. Dairy Sci., 71:2035–2043 (1988) "Physiological and Pathological Factors Influencing Bovine Immunoglobulin G2 Concentration in Milk".

Cafin et al. J. Dairy Science (1983) vol. 66, pp. 2161–2166.

Yancey R. J., Jr. J. Dairy Science (1993) vol. 76, pp. 2418–2436.

Geysen et al J. Molecular Recognition (1988) vol. 1 pp. 32–41.

Mornis et al J. Bacteriology (1985) vol. 164, pp. 255–262.

*Primary Examiner*—Paula K. Hutzell
*Assistant Examiner*—Benet Prickril
*Attorney, Agent, or Firm*—Paula J. Gaylo; David E. Boone

[57] ABSTRACT

Peptides derived from proteins associated with bacterial adherence to mammary ductile epithelium are useful in vaccine preparation for preventing mastitis. Methods for determining Microbial adherence provide rational vaccine design.

10 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Ala Val Lys Val Ala Ile Asp Gly Phe Gly Arg Ile Gly Arg Leu Ala
 1               5                   10                  15

Phe Arg Ala Ile Gln Gly
            20
```

( 2 ) INFORMATION FOR SEQ ID NO:2:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Ala Val Lys Val Ala Ile Glu Gly Phe Gly Ala Ile Gly Arg Leu Ala
 1               5                   10                  15

Phe Arg Ala Ile Gln Gly
            20
```

VACCINE DESIGN AND PRODUCTION

This application is a continuation of application Ser. No. 08/147,765, filed on Nov. 5, 1993, now abandoned.

FIELD OF THE INVENTION

The present invention provides methods for determining mechanisms of microbial adherence. The mechanisms underlying microbial adherence allow identification of the microbial molecules responsible for adherence and thus enables the design of vaccines which are useful for preventing or minimizing microbial adherence to cells, medical devices, prostheses and the like. Accordingly, the invention belongs to the fields of immunology and microbiology.

BACKGROUND OF THE INVENTION

The adherence of various bacteria and other microorganisms to specific cell types as well as to implanted devices such as prostheses, implantable defibrillators, cardiac pacemakers, artificial joints and the like poses a substantial clinical obstacle to the treatment of such infections. The antibiotic or antifungal resistance of many such adherent organisms confounds this problem.

The present invention embraces methods for determining the nature of microbial adherence through evaluation of the cell surface disparities between adherent microorganisms and non-adherent organisms. The operability and desirability of the present invention is illustrated by use of the methods recited above to determine the nature of adherence of *Staphylococcus aureus* types to bovine mammary epithelial cells thereby causing bovine mastitis. The mastitis vaccine of the present invention, which is a preferred embodiment of the invention, is illustrative of the vaccines of the invention, which are produced according to the methods of the invention.

A variety of gram positive microorganisms are known to cause mastitis. Gram positive organisms such as Streptococci, Staphylococci, and Corynebacteria are frequently implicated as the causative agents of mastitis. The tendency of a microorganism to cause mastitis has been correlated with the ability of that microorganism to adhere to the ductile epithelial cells of the bovine udder. A. J. Frost, *Infection and Immunity*, Vol. 12, No. 5, November, 1975, pp. 1554-1556.

The mastitis vaccines of the present invention take advantage of the correlation between the ability of a microorganism to adhere to the ductile epithelial cells of the bovine udder and the resultant pathogenesis. Bacterial cell walls were prepared and extracted to determine the presence of particular proteins among bacteria exhibiting adherence to ductile epithelial cells and those which lack the ability to adhere to ductile epithelial cells. The proteins present in the adherent bacteria but absent in non-adherent bacteria were then utilized to generate peptide subfragments which are the basis of the illustrative mastitis vaccines of the present invention.

SUMMARY OF THE INVENTION

The present invention provides methods for vaccine design by preparing cell wall or cell membrane extracts, determining the molecules associated with adherence by comparison of adherent versus non-adherent microbes, biochemical characterization of the adherence-related molecules, and the use of the information for rational design of vaccines, which elicit immune responses, which in turn interrupt the ability of the microbe to adhere.

A preferred embodiment of present invention provides peptide subfragments of proteins which are associated with bacterial adherence to ductile epithelial cells as well as derivatized forms thereof of the formula:

FORMULA I

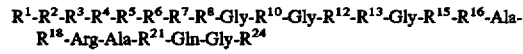

wherein $R^1$ is hydrogen or $C_1$–$C_{16}$ carboxylic acid;
$R^2$ is Ala, Gly, Ser or propionic acid;
$R^3$ is Val, Ile, Leu or D-Val;
$R^4$ is Lys or Arg;
$R^5$ is Val, Ile or Leu;
$R^6$ is Ala, Gly or Ser;
$R^7$ is Ile, Leu or Val;
$R^8$ is Asp, Asn or Glu;
$R^{10}$ is Phe, Tyr or Trp;
$R^{12}$ is Arg, Ash, Lys or His;
$R^{13}$ is Ile, Leu or Val;
$R^{15}$ is Arg, Asn, Lys or His;
$R^{16}$ is Leu, Ala, Ile or Val;
$R^{18}$ is Phe, Ash, Lys or His;
$R^{21}$ is Ile, Ala, Val or Leu;
$R^{24}$ is OH, Ala or Ser.

The present invention also provides a multiple antigenic presentation peptide of the formula:

Formula II

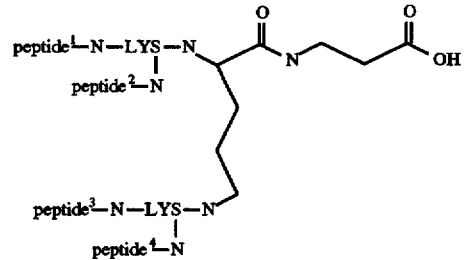

Wherein peptide[1], peptide[2], peptide[3], and peptide[4] are independently selected from the compounds of Formula I.

The present invention also provides the peptides and multiple antigenic peptides in formulations appropriate for elicitation of maximal immune responses to said peptides and said multiple antigenic presentation peptides.

DETAILED DESCRIPTION OF THE INVENTION

The effective control of bovine mastitis is critical. Dairy animals which have mastitis must be treated with antibiotics and the treatment of dairy animals with antibiotics can result in antibiotic concentrations in milk which are unacceptable under current regulatory guidelines. Accordingly, the development of an effective vaccine for bovine mastitis is of commercial importance and affords the potential for eliminating the need for antibiotic treatment in the veterinary management of mastitis. The compound of Formula I

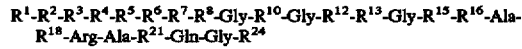

wherein $R^1$ is hydrogen or $C_1$-$C_{16}$ carboxylic acid;

$R^2$ is Ala, Gly, Ser or propionic acid;

$R^3$ is Val, Ile, Leu or D-Val;

$R^4$ is Lys or Arg;

$R^5$ is Val, Ile or Leu;

$R^6$ is Ala, Gly or Ser;

$R^7$ is Ile, Leu or Val;

$R^8$ is Asp, Asn or Glu;

$R^{10}$ is Phe, Tyr or Trp;

$R^{12}$ is Arg, Asn, Lys or His;

$R^{13}$ is Ile, Leu or Val;

$R^{15}$ is Arg, Asn, Lys or His;

$R^{16}$ is Leu, Ala, Ile or Val;

$R^{18}$ is Phe, Asn, Lys or His;

$R^{21}$ is Ile, Ala, Val or Leu;

$R^{24}$ is OH, Ala or Ser;

was derived from extensive studies aimed at determining the mechanism whereby the etiologic agents of mastitis adhere to mammary ductile epithelial cells in dairy cattle. Strains of *Staphylococcus aureus* were compared for their abilities to adhere to mammary ductile epithelial tissue and then subdivided into groups which adhered vs. those which did not adhere. Outer membrane preparations from the adherent vs. non-adherent *S. aureus* were extracted and compared for the presence of proteins found in the adherent strains but absent in the non-adherent strains. Three proteins were present in the adherent strains yet absent in the non-adherent strains. The molecular weights of these proteins were 36 KD, 47 KD, and 65 KD. The proteins were biochemically characterized and the 36 KD protein was selected as the most promising candidate for preparation of mastitis-protective vaccines. A 22 amino acid peptide corresponding to the amino terminus of the 36 KD protein was ultimately selected as the optimal immunogen for mastitis vaccine production. The natural sequence of the 22 amino acid N-terminus is preferred for purposes of vaccine preparation. Thus, in Formula I, the preferred amino acid substituents are as follows: $R^1$ is hydrogen; $R^2$ is Ala; $R^3$ is Val; $R^4$ is Lys; $R^5$ is Val; $R^6$ is Ala; $R^7$ is Ile; $R^8$ is Asp; $R^9$ is Gly; $R^{10}$ is Phe; $R^{11}$ is Gly; $R^{12}$ is Arg; $R^{13}$ is Ile; $R^{15}$ is Arg; $R^{16}$ is Leu; $R^{18}$ is Phe; $R^{21}$ is Ile; and $R^{24}$ is hydroxy. The other potential substituents of Formula I were selected based on the known biochemical and immunologic properties of amino acids having similar functional groups. The present invention also comprises immunogenic subfragments of the compound of Formula I. The multiple antigenic presentation peptide of Formula II allows presentation of multiple immunogenic peptides of Formula I and thus provides a larger molecule of immunogenic subunits which can more efficiently elicit immune responses. The peptides of Formula I presented on the multiple antigenic presentation peptide of Formula II can be the same peptide or any combination of the peptides of Formula I.

The synthesis of the peptides of Formula I can readily be carried out using solid phase protein synthesis as is well known in the art. The solid phase protein synthesis schemes of the present invention untilize common blocking groups and deprotection schemes. Notwithstanding the routine nature of solid phase peptide synthesis in the present advanced state of the art, the present inventors recommend three discourses on solid phase synthesis to facilitate the practice of the present invention. Solid-phase peptide synthesis: a silver anniversary report, Barany G. Knieb-Cordonier N., and Mullen D., Int. J. Peptide Protein Res., 30, 1987, pp 705–739; *Solid Phase Peptide Synthesis*, Stewart, J. M. and Young, J. D., Pierce Chemical Co.: Rockford, Ill., 1984; and *An Introduction to Peptide Chemistry*, Bailey, P. D., John Wiley & Sons: New York, 1992 can be consulted regarding conventional blocking groups and reaction conditions for their use, deblocking reagents and protocols, cleavage reagents and recommended conditions for their use, etc. in the event the skilled artisan has not devised preferred conditions and synthetic protocols. The present inventors utilized an Applied Biosystems automated peptide synthesizer, which is fully supplemented by the manufacturer with recommended protocols, solvents, reagents and the like. The specific protocols utilized in solid phase synthesis are detailed in the Examples.

To ensure complete understanding, certain terms and abbreviations used in the specification are defined. The term "Boc" means t-butyloxycarbonyl. The term "tosyl" is an abbreviation for p-toluene sulfonyl. The term "Chxl" is an abbreviation for cyclohexyl. The term "2Cl-Z" is an abbreviation for 2-chlorobenzyloxycarbonyl. The term "$C_1$ to $C_{16}$ carboxylic acid" means an unbranched hydrocarbon having from 1 to 16 carbons in addition to the "amino terminal" carboxylic acid. The optional $C_1$ to $C_{16}$ carboxylic acid group of Formula I is merely an amino terminal group. Accordingly, there is considerable latitude in the degree of saturation and substitutions which may occur in the $C_1$ to $C_{16}$ carboxylic acid. Examples of suitable acyclic monocarboxylic acids include: ethanoic acid ($CH_3COOH$), propanoic acid ($CH_3CH_2COOH$), butanoic acid ($CH_3(CH_2)_2COOH$), pentanoic acid ($CH_3(CH_2)_3COOH$), hexanoic acid ($CH_3(CH_2)_4COOH$), heptanoic acid ($CH_3(CH_2)_5COOH$), octanoic acid ($CH_3(CH_2)_6COOH$), nonanoic acid ($CH_3(CH_2)_7COOH$), decanoic acid ($CH_3(CH_2)_8COOH$), undecanoic acid ($CH_3(CH_2)_9COOH$), dodecanoic acid ($CH_3(CH_2)_{10}COOH$), $CH_3(CH_2)_{11}COOH$, $CH_3(CH_2)_{12}COOH$, $CH_3(CH_2)_{13}COOH$, and $CH_3(CH_2)_{14}COOH$. As discussed above unsaturated acyclical monocarboxylic acids and substituted saturated and unsaturated acyclical monocarboxylic acids may also be used. Skilled artisans will appreciate the flexibility inherent in any moiety, whose only function is to provide a termini. The compound of Formula I contains lysine residues, each of which have a reactively available amine. The amine functions of the lysines can optionally be acylated with $C_1$ to $C_{16}$ carboxylic acids. Accordingly, the present invention embraces $C_1$ to $C_{16}$ carboxylic acids and the variations discussed above.

The LYS of Formula II is an abbreviation for Lysine. The subunits ($R^2$ to $R^{24}$) of the compound of Formula I are generally L amino acids with exceptions such as propionic acid at position $R^4$ and D-Val at position $R^3$. Accordingly, the bonds between the subunits are peptide bonds. The termini of the peptides of Formulas I and II ($R^1$ and $R^{24}$) are defined to take into account the hydrogen or hydroxyl groups which would be eliminated to form a peptide bond if another amino acid was added. Thus, when $R^1$ is H, the H is not an additional H, it is the H of the respective amino acid or propionic acid of $R^2$. Likewise when $R^{24}$ is OH, the OH is not an additional OH; it is the OH of the respective amino acid of $R^{23}$. When $R^{24}$ is Ala or Ser the complete amino acid is present and the carboxy termini carboxylic acid is available for amide bond formation if the compound of Formula II is desired. The propionic acid group at $R^2$ can be either n-propionic or isopropionic.

It is preferable to express—via genetic engineering technology—the peptides of Formula I, which consist of L amino acids. Peptides of Formula I, which contain only natural amino acids would thus be most efficiently produced via genetic engineering technology utilizing the amino acid sequences and the known degeneracy of the genetic code to construct expression vectors capable of expressing large amounts of the peptides at minimal cost. The advanced state of the art in molecular biology, the commercial availability of custom DNA sequences and expression vectors for use in bacteria, yeast and mammalian cells is such that a lengthy discourse on genetic engineering is unnecessary. Artisans desiring to implement genetic engineering for production of the peptides of the invention are directed to *Molecular Cloning A Laboratory Manual* Second Edition, Sambrook, J., Fritsch, E. F., and Maniatis, T., Cold Spring Harbor Press 1989 and *Current Protocols In Molecular Biology,* Ausubel, F. M., Brent, R., Kingston, R. E., Moore, D. D., Seidman, J. G., Smith, J. A., and Struhl, K., Ed. Greene Publishing Associates and Wiley-Interscience 1989. The aforementioned resources provide an excellent technical supplement to any discourse in genetic engineering.

Formulations appropriate for elicitation of the immune response are well known in the art. Complete Freund's Adjuvant, CFA, is perhaps the best known adjuvant for elicitation of optimal immune responses. However, the presence of Mycobacteria in the Complete Freund's Adjuvant and the resultant inflammation evidenced upon repeated administration of CFA limits the utility of this adjuvant in the treatment of dairy animals. A variety of other natural and synthetic oil based adjuvants are available and readily amenable to purposes of the present invention. A brief discussion of adjuvants is provided below.

An adjuvant may be defined as any preparation that when administered simultaneously with antigen increases the immune response to the antigen. Antigens are materials which perturb a host's immune system and result in an immune response towards the offending material (the antigen).

The mechanism(s) of action of adjuvants is not completely understood, but they are believed to attract immune reactive lymphocytes to the site of antigen deposition, to localize antigens in an inflammatory site (depot effect), to delay antigen catabolism, to activate the metabolism of reactive cells, and to stimulate lymphoid cell interactions.

Adjuvants may also act by several other mechanisms such as: by binding to autoantigens and modifying them, by simply altering their configuration at the water-oil interface for Freund's adjuvant, or by nonspecific stimulation of T and or B lymphocytes.

Many adjuvants will also produce a "non-specific" increase in immune reactivity if administered without a specific antigen. Effective adjuvants include oils, mineral salts, double-stranded nucleic acids, products of microorganisms, and a variety of other agents.

The most widely known oil-based adjuvants are the complete and incomplete versions of Freund's adjuvants which were described briefly above. These adjuvants consist of a water or saline in oil (or wax) emulsion. Typically, soluble antigen is dissolved in saline and emulsified in equal parts of an oil, such as Bayol F™ (42.5% paraffin, 31.4% monocyclic naphthalene, and 26.1% polycyclic naphthalene) or Arlacel A (mannite monolate). The addition of killed Mycobacteria greatly increases the adjuvant activity and such adjuvants are designated as "complete" adjuvants as opposed to the incomplete adjuvants, which lack Mycobacteria. Other microbial products including lipid protein extracts may be substituted for the mycobacterium. The glycolipid and peptidoglycan portions (wax D) of Mycobacteria have been determined to be largely responsible for the increased adjuvant effect seen when complete adjuvants are used.

Vaccines utilizing a single emulsion adjuvant system are most effective when injected intradermally or subcutaneously. Double emulsions (aqueous in oil in aqueous) are more "free flowing" emulsions and greater latitude in route of administration is attained.

Mineral salts are another approach to increasing the immunogenicity and thus the efficacy of a vaccine. Solutions of antigens precipitated with mineral salts such as calcium phosphate, silica, alum (aluminum potassium sulfate or aluminum phosphate), or alumina cream produce granulomas at the site of injection and in the lymph nodes draining the area of injection. The immune granuloma functions similarly to those produced by Freund's adjuvant. Alum precipitated antigens have been used in man to increase the extent of an immune response to prophylactic immunization to antigens, such as diphtheria toxoid.

Insoluble colloidal carriers are another class of adjuvants. In addition to alum precipitates other colloidal carriers may be used alone or in combination with microbial products or extracts and the antigen to constitute an adjuvant. Blood charcoal has proven useful in inciting production of antibody against absorbed antigens. Calcium or sodium alginate of controlled polymer length have adjuvant properties. Polyacrylamide gel has proven to be quite efficient for inciting antibody production to small amounts of entrapped antigen. Bentonite has also been employed successfully as an adjuvant.

Methylated bovine serum albumin and other positively charged proteins are quite efficient as adjuvants when mixed with a negatively charged antigen, DNA or polynucleotide to produce a precipitate.

Microbial extracts were mentioned briefly as to their utility in adjuvants. The endotoxins such as the intracellular lipopolysaccharide of gram negative bacteria are potent in potentiating immune responses. Endotoxins can function as adjuvants when administered systematically, but are more effective if injected along with the antigen. Many of the endotoxins are capable of stimulating antibody synthesis and B cell proliferation as well as increasing phagocytic activity by macrophages. Preferred endotoxins include those from *E. coli* 0111:B4, *S. typhimurium* types, *S. enteriditis* and *S. minnesota*. The cell walls of Mycobacteria and certain fungi also enhance immune reactivity. These agents seem to attract and activate macrophages, thus increasing phagocytosis at the site of then antigen-induced inflammation which in turn results in increased antigenic display by the accessory cells which in turn increases the activation of antigen-reactive B lymphocytes as well as increases cell-mediated (T cell) functions.

Polynucleotides, especially double stranded polynucleotides such as polyinosine-polycytidylic (poly (IC)) or polyadenylic-polyuridylic acid (poly (AU)) are potent adjuvants and immunostimulatory agents. They appear to act through activation of antigen reactive T cells. Polynucleotides may also serve to activate macrophages.

*Bacillus calmette* guerin (BCG), *Corynebacterium parvum*, *Listeria monocytogenes*, and *Bordetella pertussis* or extracts of these bacteria have been used as adjuvants. Levamisole, an antihelmintic drug also functions as an adjuvant, presumably through its ability to activate T cells, increase complement levels and activate macrophages.

The choice of adjuvant or combination of adjuvants is entirely within the skills of the ordinarily skilled immunologist. The adjuvants discussed above included adjuvants useful in experimental settings as well as adjuvants of potential veterinary application. The mastitis vaccines of the invention can be formulated using any of the aforementioned adjuvants and as such the use of any of the adjuvants in combination or in conjunction with the peptides of the invention is contemplated by and is thus within the scope of the present invention.

The mastitis vaccines of the present invention have proven effective in eliciting humoral responses comprising antibodies which block the binding of otherwise adherent bacterial strains to cultured mammary epithelial cells. The immunization protocols and details for the bovine mammary epithelium cell/bacterial adherence assay are provided in the Examples. Table I presents data evidencing the effectiveness of the mastitis vaccines of the present invention to elicit humoral responses which inhibit attachment of S. aureus to the ductal epithelial cells of dairy animals.

TABLE I

| Percent Binding Inhibition | | | |
|---|---|---|---|
| | PRE | POST | BOOST |
| Control Cows | | | |
| 1 | 0 | 8 | 34 |
| 2 | 11 | 20 | 28 |
| 3 | 12 | 17 | 39 |
| Mean | 8 | 15 | 34 |
| Experimental Cows | | | |
| 1 | 10 | 35 | 58 |
| 2 | 21 | 52 | 63 |
| 3 | 0 | 41 | 58 |
| 4 | 5 | 54 | 57 |
| 5 | 10 | 38 | 51 |
| 6 | 5 | 36 | 58 |
| 7 | 2 | 46 | 55 |
| 8 | 12 | 40 | 57 |
| 9 | 12 | 36 | 59 |
| 10 | 3 | 32 | 52 |
| 11 | 0 | 55 | 54 |
| 12 | 0 | 30 | 53 |
| 13 | 12 | 45 | 57 |
| 14 | 31 | 36 | 51 |
| 15 | 17 | 46 | 51 |
| Mean | 9 | 41 | 56 |

The term "PRE" refers to the normalized pre-immunization ability of the animals sera to block adherence. "POST" reflects the post-immunization levels. "BOOST" values are the values observed following administration of the booster immunization as described in the Examples. The protocols utilized to generate the data of Table I are provided in Example 6.

The vaccines of the present invention are especially useful in the veterinary management of mastitis in dairy cattle. The adherence of bacteria to the ductile epithelial cells in the disease state of mastitis is especially susceptible to the vaccines of the present invention because the ability of the vaccines of the invention to block bacterial adherence results in the bacteria being shed in the normal course of milking.

The discussion and data provided above are directed primarily toward the preferred embodiment of the present invention, which is the use of the method of the invention to design the mastitis vaccines of the invention. Skilled artisans will recognize that the present invention in its various aspects is extrapolative to the myriad other areas where microbial adherence is problematic and thus these other applications of the invention are contemplated by and thus are within the scope of the invention.

The Examples which follow describe specific embodiments of the invention and are intended to further illustrate the invention and do not imply any limitation in the scope of the invention.

EXAMPLE 1

Synthesis of AVKVAIDGFGRIGRLAFRAIQG-OH hereinafter referred to as SEQ ID NO:1 328 mg (0.25 mM) Boc GlyOCH$_2$PAM resin (Applied Biosystems) were carried through double coupling cycles on an Applied Biosystems 430A peptide synthesizer using Boc amino acids with the following side chain protecting groups: Arg (Tosyl), Asp (Chxl), and Lys (2-Cl -Z). The N-terminal Boc group was removed from the completed peptidyl resin via a TFA deprotection cycle, the resin was then transferred to an HF reaction vessel where the excess solvent was removed and the resin dried in vacuo to yield 1.03 g. 1 mL m-cresol was added, the vessel was attached to an HF apparatus (Penninsula Labs), cooled to −78° C., evacuated and approximately 15 mL liquid hydrogen fluoride (HF) was condensed in. The reaction was stirred for 1 hour in an ice bath, then the HF was removed in vacuo and the residue was suspended in 200 mL ethyl ether. The solid material was filtered through a 60 mL glass fritted filter funnel and then washed twice with ether. The peptide was solubilized and separated from the resin by washing the collected material twice with 15 mL 50% aqueous CH$_3$COOH (aq HOAc), twice with 15 mL 10% aq HOAc, and once with 15 mL water. The combined aqueous filtrate was frozen and lyophilized. The lyophilized material was re-dissolved in 15 mL 50% aq HOAc, 10 mL 10% aq HOAc, and 3 mL CH$_3$CN. 5 uL of the solution was removed, diluted to 500 uL with 0.1% TFA and 25 uL was injected onto a 0.46×15 cm Vydac C18 column using an FPLC (Pharmacia) system for analysis. A flow rate of 0.5 ml/minute was used. The chromatography was performed at room temperature. A UV monitor with a 214 nm filter and a 0.2 A scale setting on the FPLC's monitor (Pharmacia) were used to monitor the separation. Chromatography solution A was 0.1% TFA. Chromatography solution B was 0.1% TFA/50% CH$_3$CN, and a gradient of 50% B for 5 minutes, then a 1% per minute increase in B for 40 minutes and the thusly generated 90% B solution was maintained for 5 minutes.

The remainder of the solution was loaded onto a 2.2×25 cm Vydac C18 column for preparative purification on an FPLC. A gradient of 25% B for 50 minutes, then 25 to 65% B over 450 minutes was used. 5 minute (25 ml) fractions were collected. The UV absorbance was monitored at 214 nm using a FPLC monitor scale setting of 2.0 A. 40 ul samples of various fractions from 60–74 were diluted 1:10 with 0.1% TFA and 20 uL of each was analyzed by HPLC. Fractions 64–68 were combined, frozen and lyophilized to yield 112 mg. A sample of product was subjected to amino acid analysis and mass spectrometer analysis. Amino acid molar ratios confirmed that the desired product had been obtained. Fast atom bombarbment mass spectroscopy data indicated 2 higher molecular weight components (2375.0 and 2357.4) in addition to the desired product (2315.75). HPLC analysis of the product indicated a purity of greater than 90%.

EXAMPLE 2

Large Scale Synthesis of AVKVAIDGFGRIGRLAFRAIQG-OH (SEQ ID NO:1) The synthesis, cleavage and purification proceeded in substantial accordance with the teachings of Example 1. 0.65 g (0.5 mM) Boc GlyOCH$_2$PAM resin were used in the synthesis of AVKVAIDGFGRIGRLAFRAIQG-OH and 2.1 g of completed peptidyl resin were obtained (98% of theoretical weight gain). 1.5 ml of m-cresol and 20 ml HF were used in the cleavage and 1.06 g of crude product was obtained on lyophilization of the aqueous wash of the collected solids. HPLC analysis of the product indicated approximately 75% purity and amino acid analysis showed all the predicted residues to be present. The ratio of amino acids was within the expected range for a crude peptide preparation but the variability in the ratios was somewhat higher than desired. Mass spectroscopy failed to detect a product with a mass of 2315.75. The absence of a 2315.75 MW product was attributed to the presence of Asp-Gly at positions 7 and 8 and potential Aspartimide formation on HF cleavage.

EXAMPLE 3

Synthesis of AVKVAIEGFGAIGRLAFRAIQG-OH hereinafter referred to as SEQ ID NO:2 The synthesis, cleavage and purification were performed in substantial accordance with Example 1. Positions 7 and 8 in this synthesis differ from the corresponding positions of the reaction product of Example 2. Positions 7 and 8 of this peptide were selected for compatibility with the HF cleavage aspect of the process. 650 mg (0.5 mM) of Boc GlyOCH$_2$PAM resin were carried through the desired synthesis where the side chain protection used for Glu$^7$ was Chxl. Double couplings on a ABI 430A peptide synthesizer were done as described in Example 1. 2.08 g (97%) of peptidyl resin was obtained after drying. The HF cleavage was carried out in substantial accordance with Example 2. An HPLC analysis of the aqueous wash of the collected solids was performed and the remaining 100 mL of aqueous solution was purified by preparative chromatography.

Fractions 90–107 were combined, frozen and lyophilized to give 400 mg. HPLC analysis indicated purity at aproximately 95%+. Amino acid ratios agreed with theoretical values and mass spectroscopy data confirmed the presence of the desired molecular weight (2329.78) product.

EXAMPLE 4

Synthesis of Multiple Antigenic Presentation Mastitis Peptide:
(AVKVAIDGFGRIGRLAFRAIQG)$_4$ MAPS 4-branch One gram of (0.5 mM) MAP 4-branch t-Boc resin (Applied Biosystems) was carried the same solid phase synthesis as in Example 1 on an ABI 430A peptide synthesizer using Boc amino acids with double coupling. 2.7 g of peptidyl resin was obtained on drying and 2 mL m-cresol and 25 mL liquid HF were used in the cleavage. After removal of the HF and precipitation with ether, the solids were filtered, washed with ether, and the peptide extracted from the collected solids by washing with 50% aq HOAc, with 10% aq HOAc, and with water. The combined aqueous filtrate was frozen and lyophilized to yield 830 mg. HPLC analysis indicated only a broad hump and amino acid analysis provided ratios that ranged from 68% to 127% of theoretical values. Protein content was found to be 36%. The product was used for immunizations without additional purification/characterization.

EXAMPLE 5

Formulation of the Vaccine

The preferred mastitis vaccine of the invention was prepared as a double emulsion (aqueous in oil in aqueous). The desired amount of the preferred peptide was dissolved in sterile phosphate buffered saline (PBS) containing 0.5% CaCl$_2$ and emulsified in an equivalent volume of CFA (Difco) using an Omni Corp. mixer with a micro attachment. An ice bath is used to prevent thermal damage to the peptide. An alternative albeit emulsification protocol is to use two glass syringes and a Leur lock valve to repeatedly transfer the emulsion between the two syringes. Regardless of the manner of emulsification, the emulsion should be tested for its ability to resist dispersal in an aqueous medium. Testing of the emulsion is performed by placing a drop of the emulsion on water and observing for dispersal of the emulsion. If the drop of emulsion is stable on water for a couple of minutes the emulsion is sufficient.

The peptide in PBS (the initial aqueous phase) emulsified in oil (CFA) was then emulsified in an equal volume of 2% Tween™ 80 (Sigma) using a mixer with micro attachment. Syringes with a Leur lock valve would work equally well for the emulsification.

EXAMPLE 6

Immunization Protocols

Cattle Studies

A small sample of blood was harvested from each animal prior to initiation of the immunization procedure. The prebleed values for each animal in the study are provide in Table I as PRE. All immunizations consisted of 1 mL of the indicated injectant and all injections were subcutaneous. Animals in the control group received 1 mL of PBS each time the experimental group was challenged with the vaccine. The initial immunization consisted of 50 micrograms of the preferred peptide emulsified in modified complete Freund's adjuvant as detailed in Example 5. Seven days after the initial injection, each "experimental animal" received a second injection of 75 micrograms in modified incomplete Freund's (1 mL total volume) was injected subcutaneously. The experimental animals received 100 micrograms of the preferred peptide in modified incomplete Freund's adjuvant. A boost was given 7 weeks after the initial immunization with all experimental animals receiving 100 ug of modified incomplete Freund's adjuvant. Blood samples were taken and evaluated for the presence of antibodies which could block attachment of bacteria to ductal epithelial cells, Goat Studies The exorbitant costs associated with performing studies in cattle resulted in preliminary studies being conducted in goats to document seroconversion (antibody production against the preferred peptide immunogen of the invention). The immunization protocol, bleeding schedule and results obtained therefrom is provided below.

| Week | 1 | 2 | 3 | 4 | 6 | 7 | 8 | 10 |
|---|---|---|---|---|---|---|---|---|
| vaccine injected | X | X | X | X |  | X |  |  |
| blood samples collected | X |  | X | X | X | X | X | X |
| percent inhibition in cell assay | 8.8 |  | 31 | 37 | 46 | 55 | 56 | 52 |

EXAMPLE 7

Bovine Mammary Epithelial Cell Preparation

A. Tissue Recovery

Animals were selected for normal udder activity, i.e., no disease or trauma. Euthanasia were performed using a captive bolt and the entire udders were removed. The udders were extensively washed with sterile 0.85% saline at room temperature. The udders were bisected parallel to the median ligament. Healthy tissue was harvested. The recognition of healthy tissue requires some familiarity with tissue of this type. In the event that the artisan desiring to practice this procedure is not skilled in such matters, the present inventors suggest that only tissue which is granular in appearance be harvested. The harvested tissue specimens are cut into smaller pieces until the tissue fragments will pass through a 20 gauge needle. The tissue fragments are placed in a sterile container with Hanks Balanced Salt Solution (HBSS), (GIBCO), which has been supplemented with Gentamycin and fungizone (50 ppm). HBSS is available in two varieties one of which contains Mg and Ca. The HBSS without the Mg and Ca is hereinafter referred to as HBSS-. Skilled artisans will recognize the necessity of washing surgically harvested samples with physiologically acceptable solutions containing potent antibiotics and antifungals to minimize the chances of contamination in the resultant primary cultures. Other salt solutions, antibiotics and antifungals will work and are purely a matter of choice.

B Tissue Preparation

Approximately 100 grams of tissue prepared in step A were placed in about 400 mL of fresh ice cold HBSS. The tissue was kept on ice to the extent possible during the subsequent procedures and these procedures were performed as quickly as possible. Samples of the small tissue sections were removed to a sterile dish where they were minced to a mushy consistency. Minced samples were pooled and washed with cold HBSS until the supernatant was no longer milky in appearance.

C. Digestion Procedures

An enzyme "cocktail" was prepared to digest the intracellular matrices thereby liberating the individual cells. The enzyme solution was prepared by dissolving the following components in 400 mL of HBSS- containing gentamycin and fungizone: collagenase-1.38 g.; alpha-chymotrypsin-1 g; elastase-20 mg.; hyaluronidase-1 g.; soybean trypsin inhibitor-50 mg.; and bovine serum albumin-10 g. The aforementioned reagents are available from a number of suppliers of biological reagents. Sigma Chemical Company and Worthington Biochemicals are preferred sources.

The enzyme cocktail prepared above was filter sterilized and used to digest approximately 100 g of tissue. The digestion proceeded at 37 degrees C. for approximately 45 minutes. The exact time will vary depending on temperature, mixing, size of the tissue fragments, activity of the enzymes, etc.. The present inventors recommend that aliquots of the digestion mixture be removed periodically and observed for the presence of clumps containing more than approximately 100 cells. A microscope and hemocytometer are sufficient for this purpose.

The digestion vessel was removed from the 37 degree C. water bath or incubator (water bath is preferred due to the rapidity of thermal equilibration relative to the incubator) and the liquid was decanted into a sterile beaker using a 20 mesh sieve to filter the liquid. Residual clumps containing more than about 200 cells, if any, were partially disrupted by using a rubber policeman (a syringe plunger with the rubber end in place will also work). The digestion is returned to the water bath and closely monitored to yield a preparation of acini of 50 to 100 cells per clump. Avoidance of overdigestion is essential to the viability and thus the utility of the preparation.

The flask was removed from the water bath and the liquid decanted through a sterile Cellector™ sieve (20 mesh) using a policeman if necessary to disrupt any residual clumps which did not pass through the mesh. The tissue remaining on the mesh was discarded and the cell preparation was placed in centrifuge tubes. The cells were pelleted by centrifugation, washed twice with HBSS and resuspended in Media 199 plus Earl's salts (GIBCO), containing 20% fetal calf serum and 10% dimethly sulfoxide at a cell concentration of approximately $6 \times 10^6$ cells/mL.

D. Tissue Storage

The cell preparation from step C was divided in 1 ml aliquots and placed in 2.0 ml plastic cryo vials (Sarstedt, W. Germany). The vials were pre-frozen in a -70 degree C. freezer for 24 hours then transferred to final storage in liquid nitrogen.

EXAMPLE 8

Binding Inhibition Assay

A. Mammary Epithelial Cells

Three cryo vials of mammary epithelial cell were pooled and washed three times in 40 mL PHS, pH 7.2 at 25 degrees C.

B. Bacterial Growth

One inoculation loop of a *Staphylococcus aureus* strain which had previously been determined to adhere to mammary epithelial cells was transferred to 5 mL of sterile trypticase soy broth and incubated for 20 hours at 39 degrees C. The cells were harvested by centrifugation and washed once with equal volumes of PBS. After washing, the cells were suspended at $10^6$ cells per mL in PBS.

C. Bacterial Adherence Assa

Washed mammary epithelial cells (0.5 mL of a $10^4$ cell/mL suspension) were mixed with 0.5 mL of the bacterial cell suspension prepared in step B in a sterile 12×75 mM glass tube and incubated on a shaker bath at 39 degrees C. for 30 minutes. After incubation the cell mixture was washed four times in PBS to remove any non-adhering bacteria. Smears were made, air dried, and stained with gram crystal violet stain for 15 seconds. The number of bacteria attaching to 100 epithelial cells was determined by counting the number of *Staphylococcus aureus* attached to 25 mammary cells on multiple smears.

The efficiency of the vaccines of the present invention were determined, in part, by tittering in serum from immunized animals and correlating the ability of the dilution series to inhibit attachment. Data from these studies are summarized in Table I at page 11.

We claim:

1. A mastitis vaccine peptide having the general structural formula:

$R^1$-$R^2$-$R^3$-$R^4$-$R^5$-$R^6$-$R^7$-$R^8$-Gly-$R^{10}$-Gly-$R^{12}$-$R^{13}$-Gly-$R^{15}$-$R^{16}$-Ala-$R^{18}$-Arg-Ala-$R^{21}$-Gln-Gly-$R^{24}$ wherein
$R^1$ is hydrogen or $C_1$-$C_{16}$ carboxylic acid;
$R^2$ is Ala, Gly, Ser or propionic acid;
$R^3$ is Val, Ile, Leu or D-Val;
$R^4$ is Lys or Arg;
$R^5$ is Val, Ile or Leu;
$R^6$ is Ala, Gly or Ser;
$R^7$ is Ile, Leu or Val;
$R^8$ is Asp, Asn or Glu;
$R^{10}$ is Phe, Tyr or Trp;
$R^{12}$ is Arg, Asn, Lys or His;
$R^{13}$ is Ile, Leu or Val;
$R^{15}$ is Arg, Asn, Lys or His;
$R^{16}$ is Leu, Ala, Ile or Val;
$R^{18}$ is Phe, Asn, Lys or His;
$R^{21}$ is Ile, Ala, Val or Leu; and
$R^{24}$ is OH, Ala or Ser.

2. The mastitis vaccine peptide of claim 1 wherein:
$R^2$ is Ala; $R^3$ is Val; $R^4$ is Lys; $R^5$ is Val; $R^6$ is Ala; $R^7$ is Ile; $R^8$ is Asp; $R^{10}$ is Phe; $R^{12}$ is Arg; $R^{13}$ is Ile; $R^{15}$ is Arg; $R^{16}$ is Leu; $R^{18}$ is Phe; $R^{21}$ is Ile; and $R^{24}$ is OH.

3. A multiple antigenic presentation peptide having the general structural formula:

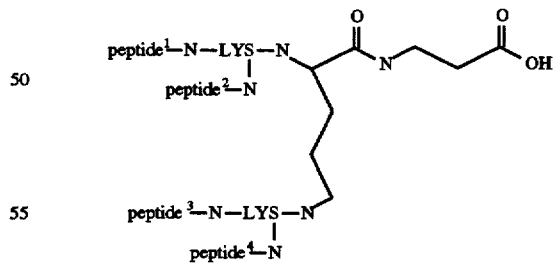

wherein: peptide[1], peptide[2], peptide[3], and peptide[4] are independently selected from the peptides of claim 1.

4. The multiple antigenic presentation peptide of claim 3 wherein peptide[1], peptide[2], peptide[3], and peptide[4] each consist of a peptide of claim 2.

5. A pharmaceutical formulation comprising the peptide of claim 1 in an adjuvant.

6. A pharmaceutical formulation comprising the peptide of claim 2 in an adjuvant.

7. A pharmaceutical formulation comprising the peptide of claim 4 in an adjuvant.

8. A mastitis vaccine peptide having the structural formula:

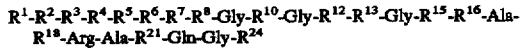

wherein $R^1$ is hydrogen or $C_1$–$C_{16}$ carboxylic acid; $R^2$ is Ala; $R^3$ is Val; $R^4$ is Lys; $R^5$ is Val; $R^6$ is Ala; $R^7$ is Ile; $R^8$ is Asp; $R^{10}$ is Phe; $R^{12}$ is Arg; $R^{13}$ is Ile; $R^{15}$ is Arg; $R^{16}$ is Leu; $R^{18}$ is Phe; $R^{21}$ is Ile; and $R^{24}$ is OH.

9. A mastitis vaccine peptide having the structural formula:

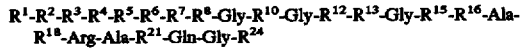

wherein $R^1$ is hydrogen or $C_1$–$C_{16}$ carboxylic acid; $R^2$ is Ala; $R^3$ is Val; $R^4$ is Lys; $R^5$ is Val; $R^6$ is Ala; $R^7$ is Ile; $R^8$ is Glu; $R^{10}$ is Phe; $R^{12}$ is Ala; $R^{13}$ is Ile; $R^{15}$ is Arg; $R^{16}$ is Leu; $R^{18}$ is Phe; $R^{21}$ is Ile; and $R^{24}$ is OH.

10. A multiple antigenic presentation peptide having the general structural formula:

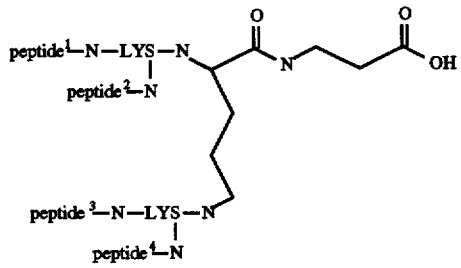

wherein peptide[1], peptide[2], peptide[3], and peptide[4] are

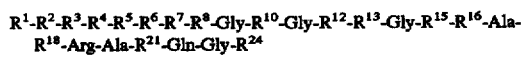

wherein $R^1$ is hydrogen or $C_1$–$C_{16}$ carboxylic acid; $R^2$ is Ala; $R^3$ is Val; $R^4$ is Lys; $R^5$ is Val; $R^6$ is Ala; $R^7$ is Ile; $R^8$ is Asp; $R^{10}$ is Phe; $R^{12}$ is Arg; $R^{13}$ is Ile; $R^{15}$ is Arg; $R^{16}$ is Leu; $R^{18}$ is Phe; $R^{21}$ is Ile; and $R^{24}$ is OH.

* * * * *